US005864633A

United States Patent [19]
Opsal et al.

[11] Patent Number: 5,864,633
[45] Date of Patent: Jan. 26, 1999

[54] METHOD AND APPARATUS FOR OPTICAL DATA ANALYSIS

[75] Inventors: Jon Opsal, Livermore; John J. Sidorowich, Aptos, both of Calif.

[73] Assignee: Therma-Wave, Inc., Fremont, Calif.

[21] Appl. No.: 649,576

[22] Filed: May 17, 1996

[51] Int. Cl.[6] .............................. G06K 9/00; G06F 15/18
[52] U.S. Cl. ............................................ 382/141; 395/13
[58] Field of Search ................................... 382/141, 142, 382/143, 144, 145, 146, 147, 148, 149, 150, 151, 152; 395/13; 250/560; 356/381, 382; 364/444, 554, 513

[56] References Cited

U.S. PATENT DOCUMENTS

| | | | |
|---|---|---|---|
| 4,999,509 | 3/1991 | Wada et al. | 250/560 |
| 5,148,513 | 9/1992 | Koza et al. | 395/13 |
| 5,222,192 | 6/1993 | Shaefer | 395/13 |
| 5,249,259 | 9/1993 | Harvey | 395/13 |
| 5,255,345 | 10/1993 | Shaefer | 395/13 |
| 5,343,554 | 8/1994 | Koza et al. | 395/13 |
| 5,394,509 | 2/1995 | Winston | 395/13 |
| 5,434,796 | 7/1995 | Weininger | 395/13 |
| 5,493,401 | 2/1996 | Horie et al. | 356/382 |
| 5,541,848 | 7/1996 | McCormack et al. | 364/478.01 |
| 5,568,590 | 10/1996 | Tolson | 359/13 |
| 5,581,657 | 12/1996 | Lyon | 395/13 |
| 5,586,218 | 12/1996 | Allen | 395/10 |
| 5,651,099 | 7/1997 | Konsella | 395/13 |
| 5,694,474 | 12/1997 | Ngo et al. | 381/66 |

OTHER PUBLICATIONS

International Search Report, mailed Sep. 29, 1997, in corresponding PCT Application No. PCT/US97/08295, International filing date Apr. 30, 1997, 4 pages in length.

R.A. Sequeira, R.L. Olson, J.L. Willers & J.M. McKinion, "Automating the parameterization of mathematical models using genetic algorithms, " *Computer and Electronics in Agriculture*, (1994), vol. 11, pp. 265–290.

E. Michielssen, S. Ranjithan & R. Mittra, "Optimal multlayer filter design using real coded genetic algorithms," *IEE Proceedings–J*, Dec. 1992, vol. 139, No. 6, pp. 413–420.

T. Eisenhammer, M. Lazarov, M. Leutbecher, U. Schöffel & R. Sizmann, "Optimization of interference filters with genetic algorithms applied to silver–based heat mirrors," *Applied Optics*, Nov. 1, 1993, vol. 32, No. 31, pp. 6310–6315.

S. Martin, J. Rivory & M. Schoenauer, "Simulated Darwinian evolution of homogeneous multilayer systems: a new method for optical coatings design," *2319 Optics Communications*, Sep. 1, 1994, vol. 110, No. 5/6, pp. 503–506.

K. Rabinovitch & G. Toker, "Genetic algorithm and thin–film design," *Proceedings SPIE*, Jul. 1994, vol. 2262, pp. 163–174.

S. Martin, J. Rivory & M. Schoenauer, "Synthesis of optical multilayer systems using genetic algorithms," *applied Optics*, May 1, 1995, vol. 34, No. 13, pp. 2247–2254.

(List continued on next page.)

*Primary Examiner*—Jose L. Couso
*Assistant Examiner*—Duy M. Dang
*Attorney, Agent, or Firm*—Limbach & Limbach L.L.P.

[57] ABSTRACT

An optical inspection device generates a plurality of measured optical data from inspection of a thin film stack. A processor evolves models of theoretical data, which are compared to the measured data, and a "best fit" solution is provided as the result. Each model of theoretical data is represented by an underlying "genotype" which is an ordered list of "genes." Each gene corresponds to a selected thin film parameter of interest. Many such individual genotypes are created thereby forming a "population" of genotypes, which are evolved through the use of a genetic algorithm. Each genotype has a fitness associated therewith based on how much the theoretical data derived therefrom differs from the measured data. Individual genotypes are selected based on fitness, then a genetic operation is performed on the selected genotypes to produce new genotypes. Multiple generations of genotypes are evolved until an acceptable solution is obtained.

15 Claims, 4 Drawing Sheets

OTHER PUBLICATIONS

T. Bäck & M. Schütz, "Evolution Strategies for Mixed–Integer Optimization of Optical Multilayer Systems," *Proceedings Fourth Annual Conference on Evolutionary Programming*, 1995, pp. 33–51.

D.J. Mikulin, D.A. Coley & J.R. Sambles, "Fitting reflectivity data from liquid crystal cells using genetic algorithms," *Liquid Crystals*, 1997, vol. 22, No. 3, pp. 301–307.

Mitchell "Genetic Algorithms: An Overview", Complexity, vol. 1, No. 1; pp. 31–39.

Koza "Introduction to Genetic Algorithms" Genetic Programming, Chapter 3.

Holland "Genetic Algorithms", Scientific American, Jul. 1992; pp. 66–72.

Riolo "Survival of the Fittest Bits" Scientific American, Jul. 1992; pp. 114–116.

J.T. Fanton, J. Opsal, D.L. Willenborg, S.M. Kelso & A. Rosencwaig, "Multiparameter measurements of thin films using beam–profile reflectometry," *Journal of Applied Physics*, 1 Jun. 1993, vol. 73, No. 11, pp. 7035–7040.

J.M. Leng, J.J. Sidorowich, Y.D. Yoon & J. Opsal and B.H. Lee, G. Cha, J. Moon & S.I. Lee, "Simultaneous measurement of six layers in a silicon on insulator film stack using spectrophotometry and beam profile reflectometry," *Journal of Applied Physics*, 15 Apr. 1997, vol. 81, No. 8, pp. 3570–3578.

E.A. Rietman & R.C. Frye, "A Genetic Algorithm for Low Variance Control in Simiconductor Device Manufacturing: Some Early Results," *IEEE Transactions on Semiconductor Manufacturing*, 2 May 1996, vol. 9, No. 2, pp. 223–229.

Tang et al., Automatic Design of optical thin–film systems— merit function and numerical optimization method, J.Opt. Soc. Am, vol. 72, No. 11, pp. 1522–1528, Nov. 1982.

METHOD AND APPARATUS FOR OPTICAL DATA ANALYSIS

FIELD OF THE INVENTION

This invention relates to a method for evaluating the formation of thin films on semiconductor substrates using optical methods, and an apparatus embodying the method.

BACKGROUND OF THE INVENTION

Optical methods for measuring samples are generally known, in particular, for semiconductor fabrication involving the formation of a stack of thin film layers on a semiconductor substrate. Such methods are considered essential for the efficient operation of modern fabrication facilities. Optical methods are desirable because they are non-destructive and the resultant optical data can be used to derive information regarding layer parameters, such as thickness, refractive index, extinction coefficient, dispersion and scattering, for up to several layers of a film stack.

One preferred approach includes the use of the OPTIPROBE® detector manufactured and sold by Therma-Wave, Inc. of Fremont, Calif., assignee herein, and described in part in one or more of the following U.S. Pat. Nos.: 4,999,014; 5,042,951; 5,181,080 and 5,412,473, each of which is incorporated herein by reference.

Conventional optical processing technology typically relies upon using a non-linear least squares algorithm to fit the measured data to a set of data points with a solution representing specific parameters of a thin film stack.

Improvements in optical technologies can provide an ever-increasing number of measured data points, which in turn provide the opportunity for deriving layer parameters on more complicated film stacks. However, this opportunity also presents a more complex optimization problem for developing solutions based on the observed data, and conventional processing techniques (such as least squares algorithms) are proving inadequate to handle the increased complexity.

Genetic Algorithms (GA's) have been applied to the problem of adaptive function optimization. A basic theoretical framework for GA's is described in Holland, *Adaptation in Natural and Artificial Systems* (1975). The terminology used by Holland is borrowed from genetics. Thus, in the computer analog, a GA is a method for defining a "population" of solutions to a selected problem, then evolving new populations by using probabilistic genetic operations to act on "individual" members of the population, i.e. individual solutions. Each individual in the population has a plurality of "genes," which are each representative of some real parameter of interest. For example, if there are x data parameters of interest, each individual would have x genes, and populations of individuals having x genes would be propagated by a GA.

The use of GA's for function optimization is generally described in U.S. Pat. No. 5,222,192 and U.S. Pat. No. 5,255,345, both to Schaefer. Further, U.S. Pat. No. 5,394,509 to Winston generally describes the application of GA's to search for improved results from a manufacturing process. Also, there has recently been much interest in the use of GA's in the design of various types of optical filters. See Eisenhammer, et al., *Optimization of Interference Filters with Genetic Algorithms Applied to Silver-Based Heat Mirrors, Applied Optics*, Vol. 32 at pp. 6310–15 (1993); and Bäck & Schültz, *Evolution Strategies for Mixed-Integer Optimization of Optical Multilayer Systems, Proceedings of the Fourth Annual Conference on Evolutionary Programming* at pp. 33–51 (1995).

However, no one has heretofore applied GA's to the problem of evaluating thin films on semiconductor wafers, and it would be desirable to do so.

SUMMARY OF THE INVENTION

A method for using optical inspection of thin film layers formed on a semiconductor substrate to evaluate the physical characteristics of the thin film layers is disclosed. According to the method, an optical inspection device generates a plurality of measured optical data from inspection of the film stack. A processor generates sets of theoretical parameters corresponding to potential solutions of the actual parameters of the sample.

Each individual candidate model of theoretical parameters is represented as a "genotype" which is an ordered list of "genes." Each gene corresponds to a selected thin film parameter of interest.

Many such individual genotypes are created thereby forming a "population" of genotypes, which are evolved through the use of a genetic algorithm. Using conventional Fresnel equations, the processor derives theoretical data from the theoretical parameters defining each of the genotypes. The derived theoretical data for a given genotype are compared with the actual measured data in accordance with a fitness function. The fitness function provides a measure of how close the derived theoretical data are to the measured data. Individual genotypes are then selected based, in part, on this fitness comparison. One of a variety of different types of genetic operations is performed on the selected genotype to produce a new genotype. Multiple generations of genotypes are evolved until an acceptable solution is obtained. The underlying genotype associated with the theoretical data having a best "fit" with the measured data will define the most likely parameters of the thin film under investigation.

A better understanding of the features and advantages of the present invention will be obtained by reference to the following detailed description of the invention and accompanying drawings which set forth an illustrative embodiment in which the principles of the invention are utilized.

DETAILED DESCRIPTION OF THE INVENTION

Figure 1:
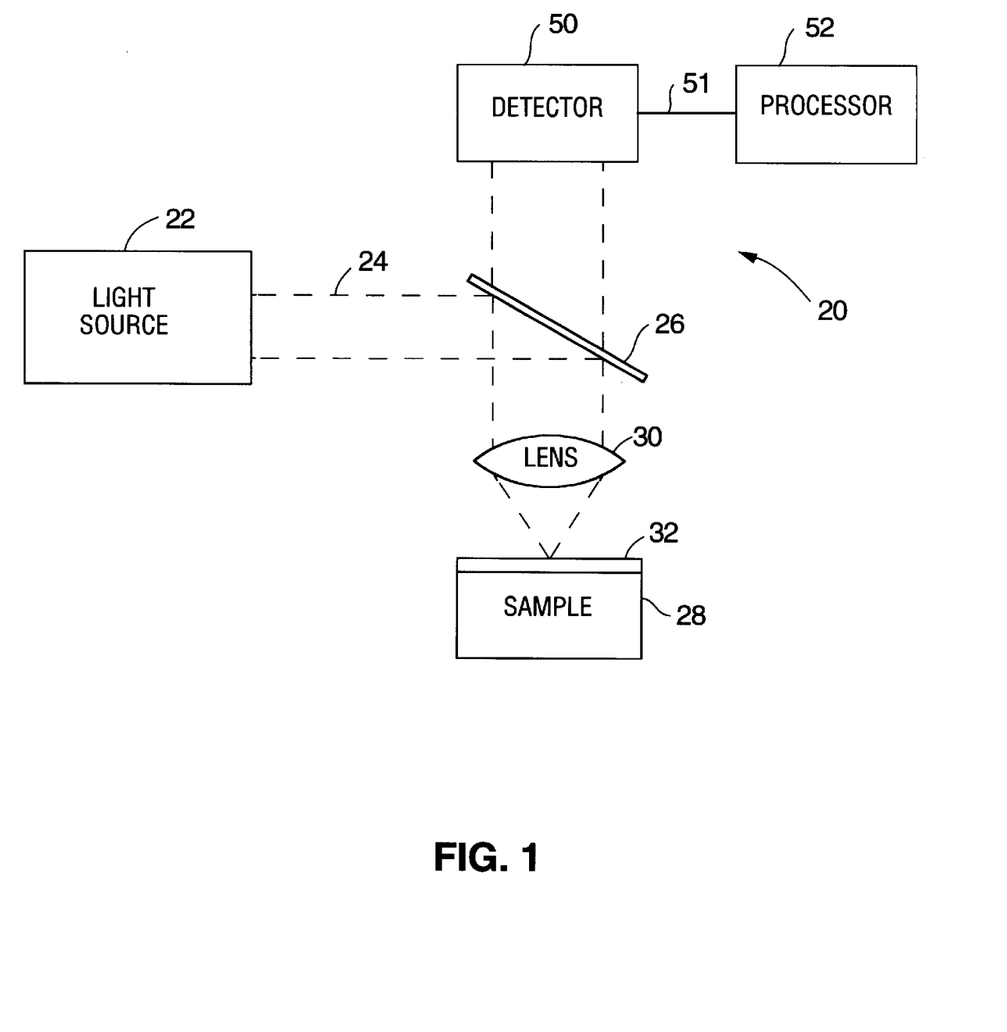
FIG. 1 is a block diagram illustrating a simplified optical inspection system.

FIG. 1 illustrates a block diagram for a basic optical inspection system 20 for measuring optical characteristics of a sample 28, such as a semiconductor wafer having one or more thin film layers 32 formed thereon. A light source 22 generates a probe beam of light 24 which is reflected by beam splitter 26 through lens 30 onto the sample 28. It should be recognized that light source 22 would preferably include any large number of wavelengths. The probe beam of light 24 is reflected off the sample 28 back through lens 30 and beam splitter 26 onto a photodetector 50. Photodetector 50 generates a plurality of outputs 51 which are supplied to a processor 52. The outputs are used to evaluate physical characteristics of the sample, and more particularly, of the thin film layer 32 of the sample.

It will be appreciated by those skilled in the art that many configurations for an optical inspection system are possible, such as those described in U.S. Pat. No. 4,999,014, U.S. Pat. No. 5,042,951, U.S. Pat. No. 5,181,080, and U.S. Pat. No. 5,412,473, each of which is incorporated herein by reference. The preferred optical inspection system employs the OPTIPROBE detector manufactured and sold by Therma-Wave, Inc. of Fremont, Calif. These patents describe how measurements may be taken at multiple wavelengths and at multiple angles of incidence either simultaneously or serially. However, for the purpose of the present invention, it is sufficient to have an optical inspection system which generates multiple optical data measurements from the inspection of the semiconductor wafer.

The optical data measurements will typically take the form of amplitude information, such as reflectance versus angle of incidence, or reflectance versus wavelength, or polarization phase information, such as provided by ellipsometry. For example, the OPTIPROBE detector uses each of these techniques to take a large number of measurements in a single scan, then it filters the measured data resulting in from tens to hundreds of data points for each set of reflectance measurements for use in measurement calculations.

Well known Fresnel equations can be used to predict or model the optical measurements expected from a known stack of layers with specified thicknesses, reflection indices and extinction coefficients. See Born & Wolf, *Principles of Optics*. However, the Fresnel equations associated with these models cannot be easily used in reverse, to unambiguously determine the various parameters of a thin film stack from a large number of multiple measured data points.

This problem is addressed in the subject invention by first generating a set of "theoretical" parameters which might correspond to the actual parameters of the stack to be evaluated. The processor, using the Fresnel modeling equations, then derives a set of theoretical data based on these theoretical parameters. The derived theoretical data are then compared to the measured data and if there is a reasonable level of correspondence, one can assume that the generated theoretical parameters fairly describe the parameters of the thin film stack under investigation.

Of course, it would be highly unlikely that the first set of generated theoretical parameters, and the associated derived theoretical data, would provide a good match to the actual measured data. In the practice of the invention, the processor will generate many thousands of sets of theoretical parameters. In accordance with the subject invention, the steps of generating the multiple sets of theoretical parameters is performed using a genetic algorithm.

Figure 2:
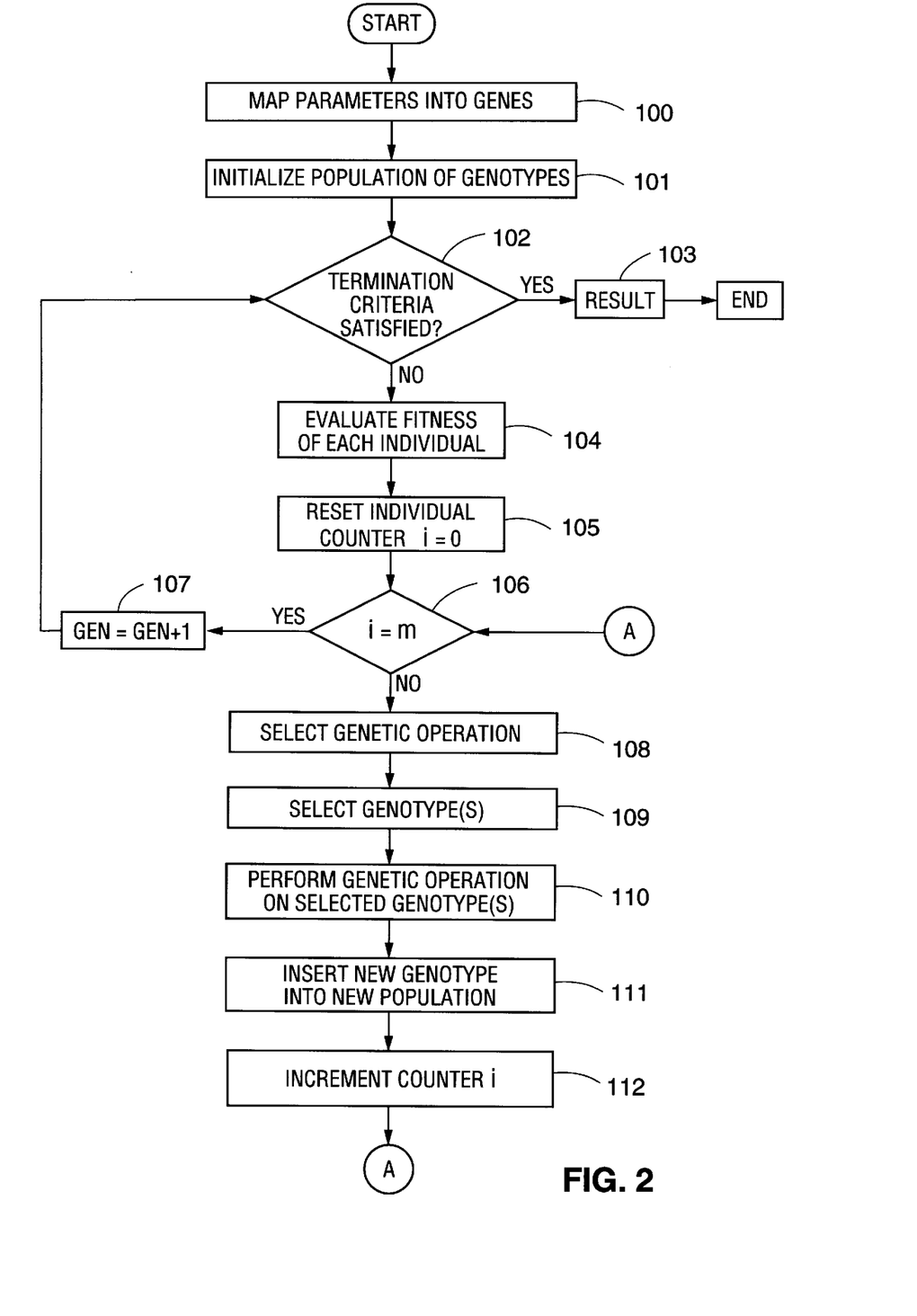
FIG. 2 is a flow chart illustrating the method of the present invention.

Referring now to FIG. 2, a flow chart illustrates one embodiment of a genetic algorithm (GA), which may be implemented in processor 52 with suitable programming, to carry out the method of the present invention. It should be recognized that many variations in methodology could be used without affecting the scope of this invention. Processor 52 can be any general purpose computer having adequate computing resources for performing iterative processing. For example, we have programmed a PENTIUM processor running the NEXTSTEP operating system in accord with the illustrated flow chart and obtained an excellent fit for data representing multi-layered stack solutions.

In step 100, the set of thin film parameters to be measured are chosen and mapped into a genotype, i.e., the physical parameters of interest are mapped into a mathematical space. A genotype is defined as an ordered list of genes, each gene representing a different thin film parameter of interest. In practical terms, each parameter of interest or gene can be mapped into an individual data store, its range specified, and its contents supplied, altered, or otherwise operated on in accord with suitable programming. The collection of individual data stores which store all the parameters of interest for a set of measurements form an individual genotype.

Figure 3A:
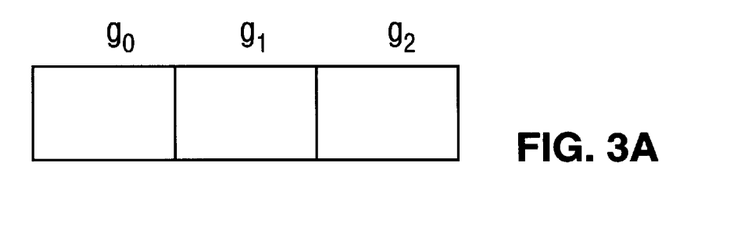
FIGS. 3a and 3b are block diagrams illustrating a memory allocation for use in the present invention.
Figure 3B:
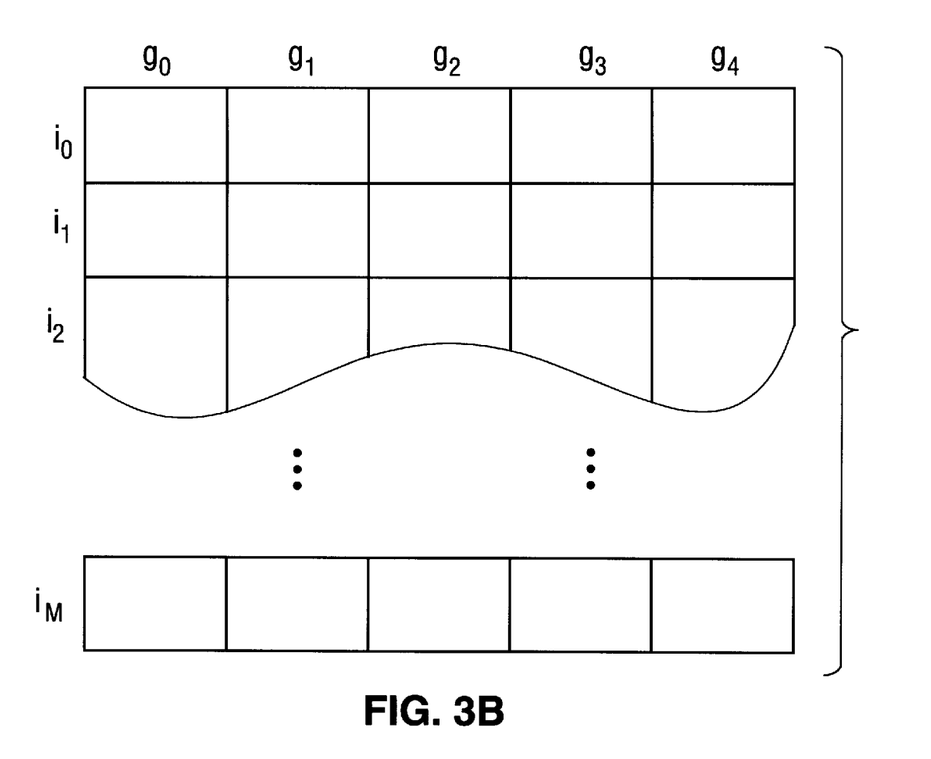

For example, a simple genotype having three parameters of interest may be mapped as shown in FIG. 3a, wherein thickness is mapped into gene $g_0$, refractive index is mapped into gene $g_1$ and extinction coefficient is mapped into gene $g_3$. It should be recognized that many different genotype configurations are possible and are created in this step according to the need as dictated by the product specification. For example, a five parameter genotype is shown in FIG. 3b, which may be mapped as follows: thickness of the first film layer is mapped into gene $g_0$, refractive index of the first film layer is mapped into gene $g_1$, extinction coefficient of the first film layer is mapped into gene $g_2$, thickness of the second film layer is mapped into gene $g_3$ and thickness of the third film layer is mapped into gene $g_4$. It is generally desirable to have parameters related to the same layer grouped together in the data store, as shown, although a different ordering may be warranted depending on the application. It can be appreciated that the genotypes may be handled with common data processing commands to operate on the information stored therein for any suitable purpose. The present invention employs a GA to operate on selected genes to propagate additional genotypes having generally increasing fitness.

In step 101, an initial population comprising M individual genotypes is created either by random or arbitrary means. For example, the initial population may be initialized with preexisting data from prior measurements. The variable GEN is used to identify the generation number and initialized to zero.

In step 102, termination criteria are examined, and if the criteria are satisfied, a preferred solution results in step 103 and the routine ends, as will be described below.

If the termination criteria are not satisfied, then the fitness of each genotype in the current population is evaluated and stored for reference in step 104. The fitness is determined by a fitness function F, which is based on the parameters of interest. In the most general example, fitness F is defined as a function of the residual value between a measured data point $x_i$ and a theoretical data point $y_i$, for N measurements, for example:

$$F = f(RES), \text{ e.g.}$$

$$2 - \sqrt{RES}$$

where $$RES = \frac{1}{N} \sqrt{\sum_{i=1}^{N} (x_i - y_i)^2}$$

In step 105, a counter i is reset to zero. The counter i counts the number of genotypes which are created in the new population. Since in this part of the routine a new population of M genotypes is being propagated, counter i is initialized and thereafter acts as a counter to track the number of genotypes which are genetically propagated in the bottom portion of the routine.

In step 106, the counter i is compared to the preset value M. If equal, then the new population is full and the generation number GEN is incremented by one in step 107. The routine then returns to step 102 to either terminate or begin constructing the next generation of genotypes. If the new population is not full, the routine proceeds to step 108 and evolves one or more new genotypes for the new generation.

In step 108, a genetic operation is selected. The selection will usually be made probabilistically, but it could be random or arbitrary. There are three basic genetic operations, namely direct reproduction, crossover and mutation, as illustrated in FIG. 4, although the invention is not strictly limited in this sense. Each of these genetic operations should be employed to some degree to provide an adequate random evolution of the data, although it is not strictly required.

For each of the three possible genetic operations, either one or two genotypes are selected from the current population. The genotype selected in step 109 is statistically based upon how close the theoretical data associated with that genotype "fits" with the measured data. Although the selection is by chance, it is more likely that a genotype having a high fitness F will be selected than one having a low fitness. In the preferred embodiment, the likelihood of being selected is directly proportional to the fitness. By selecting the genotypes in this Darwinian fashion, the population can evolve in a manner so that the genotypes migrate towards progressively better fitting solutions. In addition, by using a weighted, but still random selection process, it is possible to search for best fit solutions over the entire population. This provides a more global form of search which cannot be achieved using non-linear least square fitting algorithms that rely on narrow search strategies.

The chosen form of genetic operation will be carried out in step 110. The new genotype(s) created by the genetic operation are then written into the new population in step 111, and the counter i is incremented in step 112.

Figure 4A:
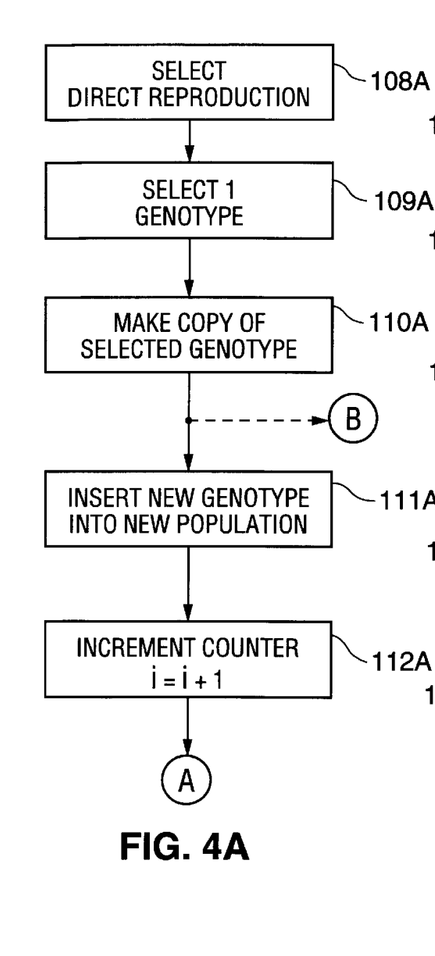
FIGS. 4a through 4c are flow chart portions illustrating the use of different genetic operations.
Figure 4B:
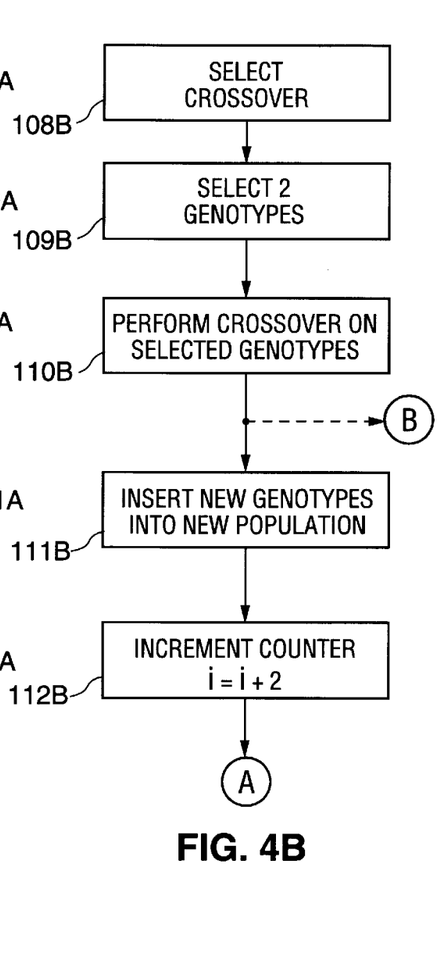
Figure 4C:
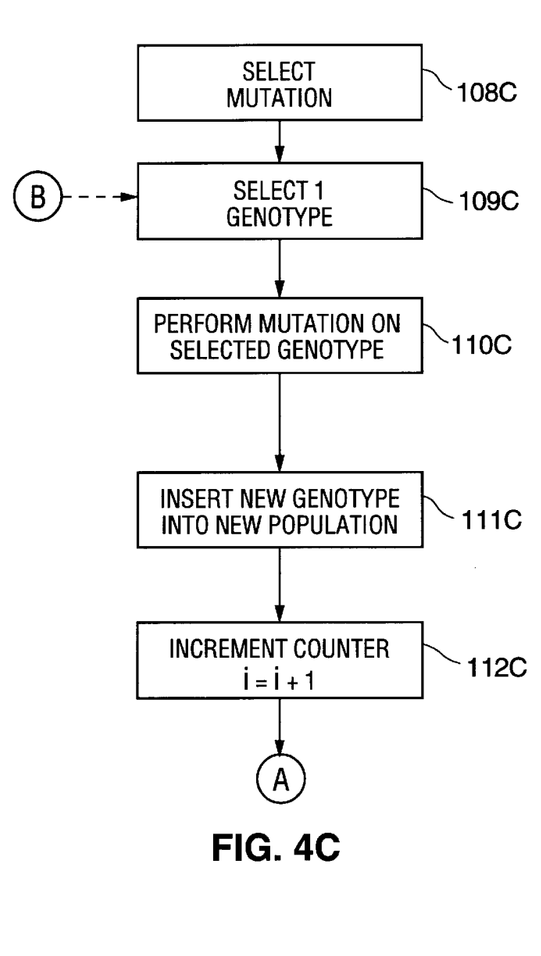

Steps 109 through 112 may be carried out in many different ways without departing from the scope of the invention. For example, the three basic genetic operations are illustrated in FIGS. 4a–4c. If direct reproduction is chosen in step 108a, a single genotype is selected in step 109a. As noted above, this selection is random, but weighted based on fitness. In step 110a, an exact copy of that selected genotype is copied and inserted into a new population (step 111a). The individual counter i is then incremented in step 112a and the routine returns to step 106 to propagate more genotypes until the new population is full. Alternatively, the exact copy of the selected genotype may be subjected to genetic mutation before being copied into the new population, as indicated by the dotted line connection B to step 109c.

If crossover is selected in step 108b, then two genotypes are randomly chosen from the current population (step 109b) based on their fitness. Crossover is then carried out in step 110b, meaning that genes from each of the selected genotypes are selected and exchanged, thereby forming two new genotypes which are then written into the new population in step 111b. If crossover is selected, the individual counter i must be incremented twice in step 112b since two new genotypes are evolved. The routine returns to step 106 to propagate more genotypes until the new population is full. Alternatively, the crossover genotypes may be subjected to genetic mutation before being copied into the new population, as indicated by the dotted line connection B to step 109c.

If mutation is selected, then one genotype is chosen from the current population in step 109c based on its fitness. Some number of genes from the selected genotype are selected and then mutated in step 110c, and the new genotype is written into the new population in step 111c. The individual counter i is then incremented in step 112 and the routine returns to step 106 to propagate more genotypes until the new population is full.

As noted above, the selection of genotypes for use in the genetic operation is generally random in proportion to fitness, although it is possible to force a selection through direct intervention. Also, the selection of individual genes to be operated upon is generally random.

As previously discussed, the routine will run until a termination criterion is satisfied in step 102. In practice, the termination criterion is designed to allow the population to evolve for a predetermined number of generations M. In this case, M can be selected based on how fast the processor runs and how long the operator is willing to wait for a result. It should be understood that the longer the populations are allowed to evolve, the more likely it is that a good fit will be obtained. Other termination criteria could be established, such as when the fitness of the best genotype of the population does not improve by at least some selected amount $\delta$ over the last Q generations. When the termination criteria is satisfied, an individual genotype having the best fitness will be selected from all the populations as the best fit for the measured data, i.e., the most representative of the physical characteristics of the measured thin film layers.

It should be understood that the invention is not intended to be limited by the specifics of the above-described embodiment, but rather defined by the accompanying claims.

We claim:

1. A method for evaluating parameters of a stack of thin film layers on a sample comrprising:

identifying a group of thin film parameters to be evaluated;

defining a genotype as a collection of genes, each gene corresponding to a selected one of the group of thin film parameters to be evaluated;

defining a population as a collection of genotypes;

initializing a current population with theoretical parameters corresponding to the actual parameters of the thin film layers to be evaluated;

for each group of theoretical parameters, deriving a set of theoretical data corresponding thereto;

optically inspecting the thin film stack and generating therefrom a set of measured data; and comparing the set of measured data to the sets of derived theoretical data for each genotype to determine a level of fitness for each genotype;

evolving a next population by selecting at least one genotype from the current population based on the fitness level of the genotype and performing a genetic operation on the at least one genotype, thereby creating at least one new genotype and adding the at least one new genotype to the next population; and repeating the comparing and evolving steps so that the theoretical thin film parameters of the selected genotype become increasingly more representative of the actual thin film parameters of the sample.

2. The method of claim 1 wherein the likelihood of selecting a genotype from the current population is proportional to how close the derived theoretical data associated with that genotype matches the measured data.

3. The method of claim 1, wherein the level of fitness of a genotype is determined by calculating the fitness as a function of the difference between the theoretical data and the measured data.

4. The method of claim 1, wherein the performing step includes reproducing an identical copy of the at least one genotype.

5. The method of claim 1, wherein the performing step includes selecting a gene from the at least one genotype and mutating the gene.

6. The method of claim 5, wherein the step of selecting a gene includes randomly selecting the gene.

7. The method of claim 1, wherein the performing step includes selecting corresponding genes in a pair of genotypes and exchanging the genes.

8. The method of claim 7, wherein the step of selecting corresponding genes includes randomly selecting the genes.

9. A method for evaluating parameters of a stack of thin film layers on a sample, comprising:

identifying a group of thin film parameters to be measured;

mapping the thin film parameters into a genotype, said genotype comprising a plurality of genes, each gene being correlated to a respective one of the group of thin film parameters to be measured;

defining a population of genotypes;

deriving a set of theoretical data for each genotype based on the parameters in each genotype;

optically inspecting the thin film stack and generating therefrom a set of measured data;

comparing the set of derived theoretical data associated with each genotype to the set of measured data and assigning a fitness to each genotype based on the comparison;

evolving a new population of genotypes by selecting at least one genotype from the current population based on the fitness of the genotype and performing a genetic operation on the at least one genotype to form at least one new genotype, said genetic operation being selected from one of the following: reproducing an identical copy of the at least one genotype; selecting a gene from the at least one genotype and mutating the gene; or selecting corresponding genes in a pair of genotypes and exchanging the genes, and adding the at least one new genotype to a next population; and repeating the comparing and evolving steps to select the genotype associated with the set of theoretical data having a best fit with the set of measured data, with the thin film parameters of the selected genotype being increasingly more representative of the actual thin film parameters on the sample.

10. The method of claim 9, wherein the step of selecting at least one genotype includes selecting at least one genotype in proportion to its fitness.

11. The method of claim 9, wherein the step of selecting a gene includes randomly selecting the gene.

12. The method of claim 9, wherein the step of selecting corresponding genes includes randomly selecting the genes.

13. A system for evaluating parameters of a layer or layers of thin film stack on a sample, comprising:

an optical system for inspecting the stack and generating therefrom a set of measured data; and a processor for generating a population of genotypes, each genotype having a collection of genes, each gene corresponding to a theoretical thin film parameter said theoretical parameters corresponding to the actual parameters of the thin film layers to be evaluated and deriving sets of theoretical data corresponding to each genotype, said processor comparing the derived sets of theoretical data for each genotype to the measured data to determine a level of fitness for each genotype, said processor evolving a new population of genotypes by selecting at least one genotype from the current population based on the fitness level of the genotype and performing a genetic operation on the at least one genotype and adding the at least one new genotype to a next population, said processor further selecting the genotype having a set of theoretical data which best matches the measured data, with the theoretical thin film parameters of the selected genotype being increasingly more representative of the actual thin film parameters associated with the sample.

14. The system of claim 13, said processor including a plurality of memory stores organized into populations, each population having a plurality of genotypes, each genotype having a plurality of genes, wherein each gene is an individual memory store correlated to a respective one of the thin film parameters, and wherein said processor functions to evolve a plurality of populations by performing genetic operations on at least one selected genotype.

15. The system of claim 14, wherein the processor further functions to perform various operations including reproducing an identical copy of the at least one genotype, selecting a gene from the at least one genotype and mutating the gene, and by selecting corresponding genes in a pair of genotypes and exchanging the genes.

* * * * *

UNITED STATES PATENT AND TRADEMARK OFFICE
CERTIFICATE OF CORRECTION

PATENT NO. : 5,864,633
DATED : January 26, 1999
INVENTOR(S) : Jon Opsal et al.

It is certified that error appears in the above-identified patent and that said Letters Patent is hereby corrected as shown below:

In Col. 3, line 29, please delete "reflection" and replace with --refractive--.

In Col. 4, lines 56-59, please delete the equation

$$RES = \frac{1}{N} \sqrt{\sum_{i=1}^{N} (x_i - y_i)^2}$$

and replace the equation with

$$RES = \sqrt{\frac{1}{N} \sum_{i=1}^{N} (x_i - y_i)^2}$$

In Col. 6, line 34, please delete "comrprising" and replace with --comprising--.

Signed and Sealed this

Twenty-ninth Day of June, 1999

Attest:

Attesting Officer

Q. TODD DICKINSON

Acting Commissioner of Patents and Trademarks